US012417857B2

(12) United States Patent
Kozin

(10) Patent No.: US 12,417,857 B2
(45) Date of Patent: Sep. 16, 2025

(54) X-RAY SHIELDING DEVICE

(71) Applicant: Lumafield, Inc., Cambridge, MA (US)

(72) Inventor: Simon Edward Kozin, Lexington, MA (US)

(73) Assignee: Lumafield, Inc., Cambridge, MA (US)

( * ) Notice: Subject to any disclaimer, the term of this patent is extended or adjusted under 35 U.S.C. 154(b) by 279 days.

(21) Appl. No.: 18/226,042

(22) Filed: Jul. 25, 2023

(65) Prior Publication Data

US 2025/0037891 A1    Jan. 30, 2025

(51) Int. Cl.
*G21F 1/12* (2006.01)
*G01N 23/046* (2018.01)
*G21F 3/00* (2006.01)

(52) U.S. Cl.
CPC .......... *G21F 1/125* (2013.01); *G01N 23/046* (2013.01); *G21F 3/00* (2013.01); *G01N 2223/505* (2013.01)

(58) Field of Classification Search
CPC .......... A61B 6/107; A61B 6/032; A61B 6/06; A61B 6/4291; A61B 6/44; A61B 6/4035; A61B 6/405; A61B 6/4405; A61B 6/4441; A61B 6/467; A61B 6/487; A61B 6/54; A61B 6/56; A61B 6/4233; A61B 5/4312; A61B 6/485; A61B 6/4417; A61B 6/502; A61B 5/0091; A61B 6/5247; A61B 6/0414; A61B 6/508; G21F 1/125; G21F 3/00; G21F 1/12; G21F 1/085; G01N 23/046; G01N 2223/30; G01N 2223/505; G01N 23/04; G01N 2223/401; G01N 2223/615;

(Continued)

(56) References Cited

U.S. PATENT DOCUMENTS 5,883,394 A    3/1999  Mussman
5,937,028 A *  8/1999  Tybinkowski ....... G01N 23/046
                                                        378/4

(Continued)

FOREIGN PATENT DOCUMENTS

CN          106169315 B   10/2017
WO     WO 2023/091435     5/2023

OTHER PUBLICATIONS

International Search Report and Written Opinion in International Appln. No. PCT/US2024/039510, mailed on Jan. 9, 2025, 21 pages.

(Continued)

*Primary Examiner* — Irakli Kiknadze
(74) *Attorney, Agent, or Firm* — Fish & Richardson P.C.

(57) ABSTRACT

An X-ray device includes: an X-ray source configured to emit X-rays; a scintillator, the scintillator being configured to emit light in response to absorption of the X-rays; a detector; a frame enclosing the X-ray source and the detector; standoffs positioned on the frame; shielding panels comprising lead; one or more brackets with fasteners configured to attach to the standoffs; and exterior panels with fasteners configured to attach to the one or more brackets. The standoffs form a datum structure for the one or more brackets. Each of the standoffs has a length and a cross-sectional size, and each of the shielding panels includes holes having a cross-sectional size greater than the cross-sectional size of the standoffs by an amount that ensures the standoffs will pass through the holes. The length of the standoffs is greater than a maximum thickness possible for the given shielding panel due to variations in thickness.

20 Claims, 12 Drawing Sheets

(58) Field of Classification Search
CPC ...... G01N 21/255; G01N 21/85; G01N 21/93; G01N 23/06; G01N 23/083; G01N 23/087; G01N 23/10; G01N 23/12; G21K 1/02; G21K 1/025; G21K 1/10; H01J 35/16; H01J 2235/165; H01J 35/02; H01J 35/20; H01J 35/06; H01J 5/22; H01J 2235/16; H01J 2235/068; H01J 35/066; H05G 1/54; H05G 1/52; G01T 1/20; G01T 1/2002; G01T 1/2018; G01T 1/24; G01T 7/00; H04N 5/321; G06T 2207/20048; G01J 3/02; G01J 3/28
See application file for complete search history.

(56) References Cited

U.S. PATENT DOCUMENTS

| | | | | |
|---|---|---|---|---|
| 7,151,817 | B1 * | 12/2006 | Abraham | G01V 5/22 378/57 |
| 8,540,425 | B2 * | 9/2013 | Nielsen Groot | A61B 6/107 378/203 |
| 2014/0126689 | A1 * | 5/2014 | Hara | A61B 6/4405 378/19 |
| 2023/0148975 | A1 | 5/2023 | Damiano et al. | |

OTHER PUBLICATIONS

Artemisshielding.com [online], "Artemis Shielding products are lead-free, non-toxic, and more durable than its lead counterpart, making it an easy decision to choose Artemis.," upon information and belief, available no later than Jun. 2023, retrieved on Oct. 26, 2023, retrieved from URL<https://artemisshielding.com/why-artemis/>, 11 pages.

Moeller-aerospace.com [online], "What is a Datum Structure?," Mar. 31, 2022, retrieved on Jul. 6, 2023, retrieved from URL<https://www.moeller-aerospace.com/datum-structure/d>, 8 pages.

* cited by examiner

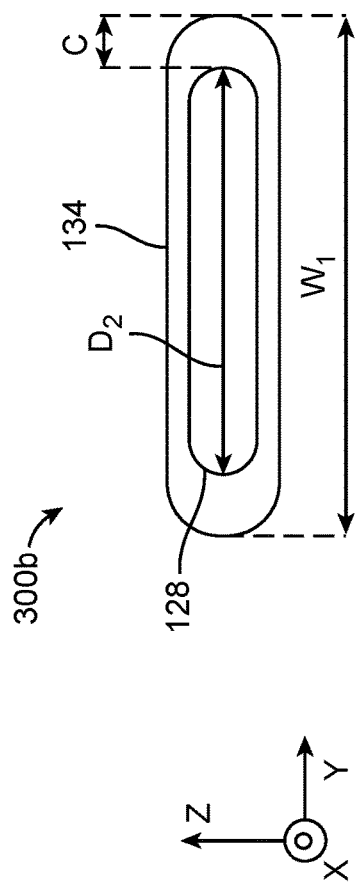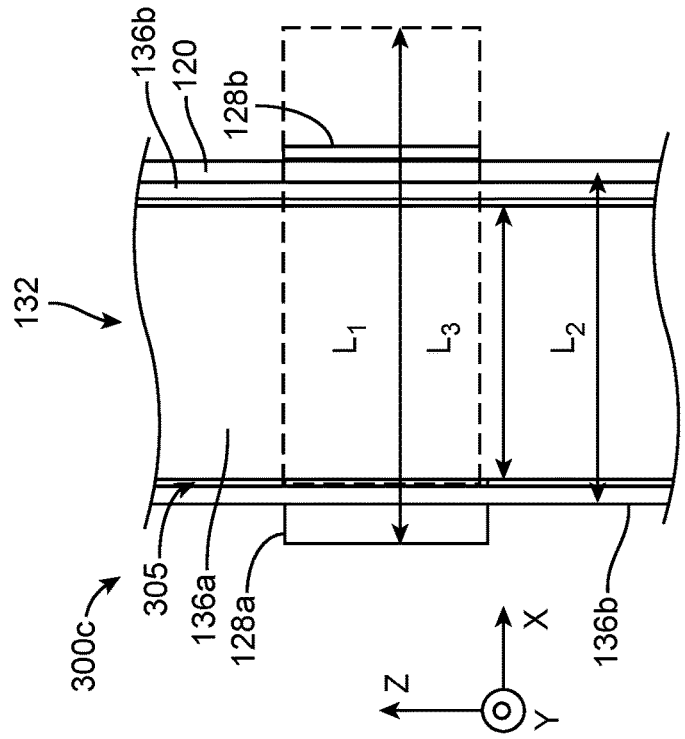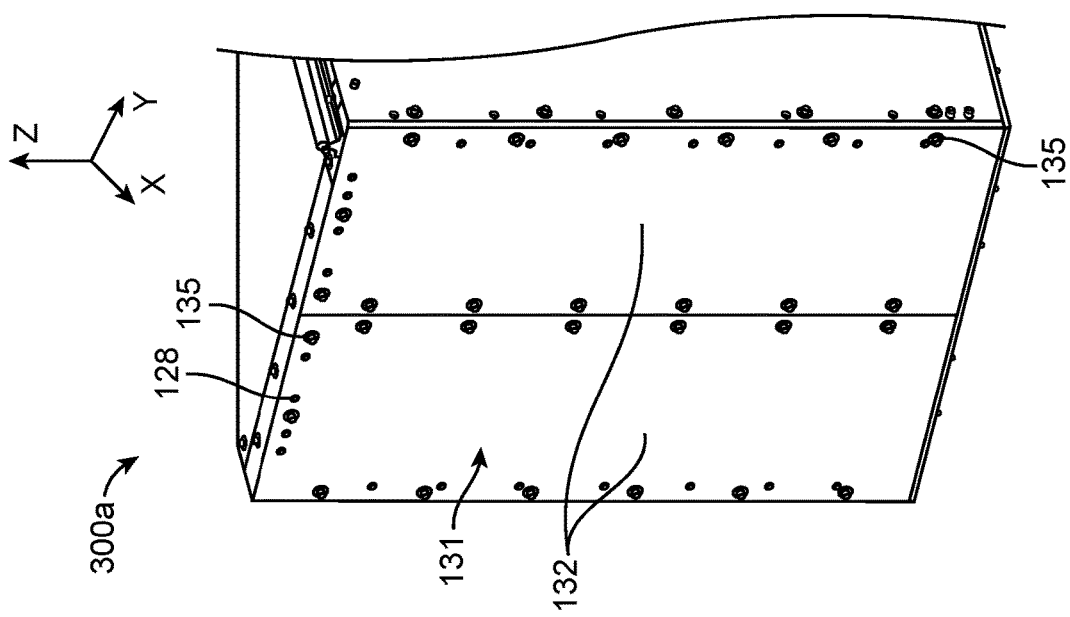
FIG. 3B
FIG. 3C
FIG. 3A

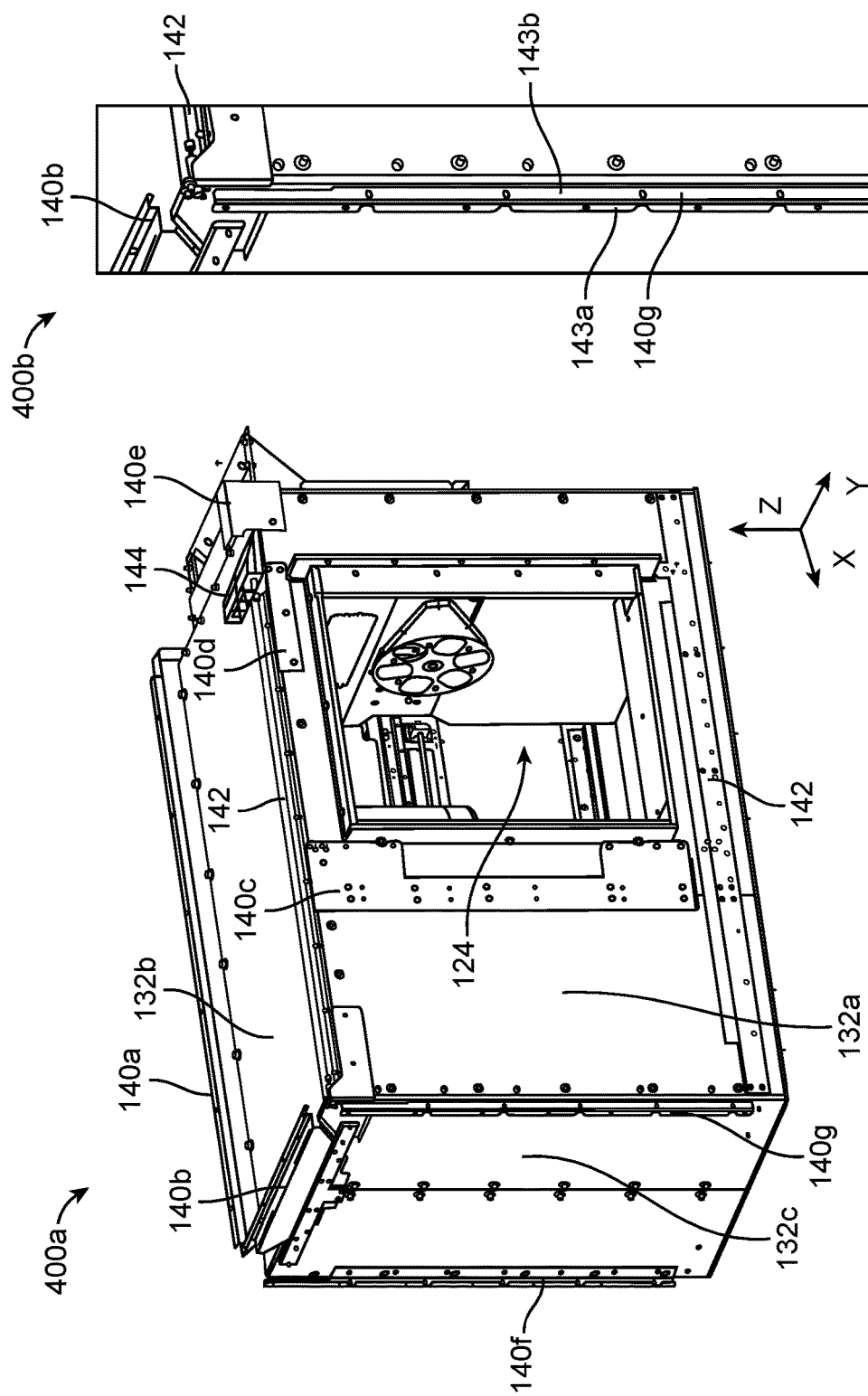

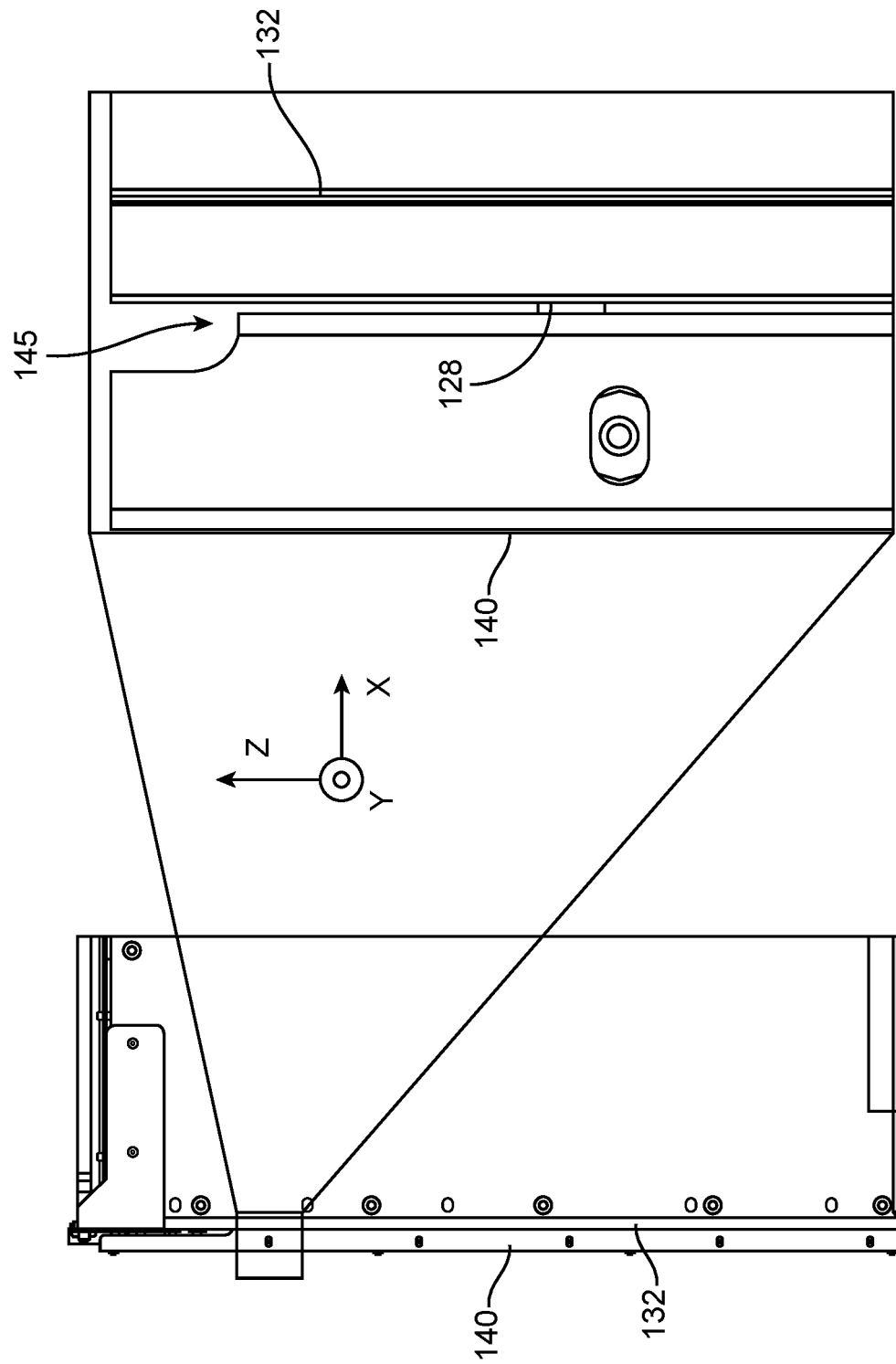

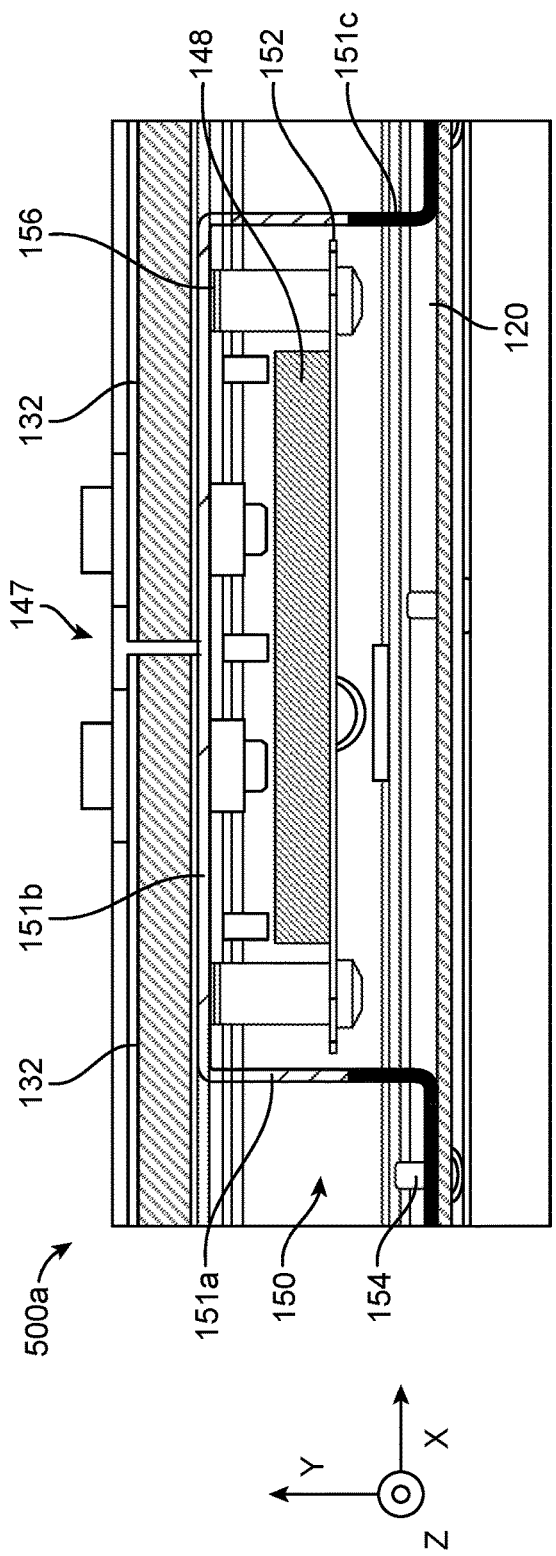
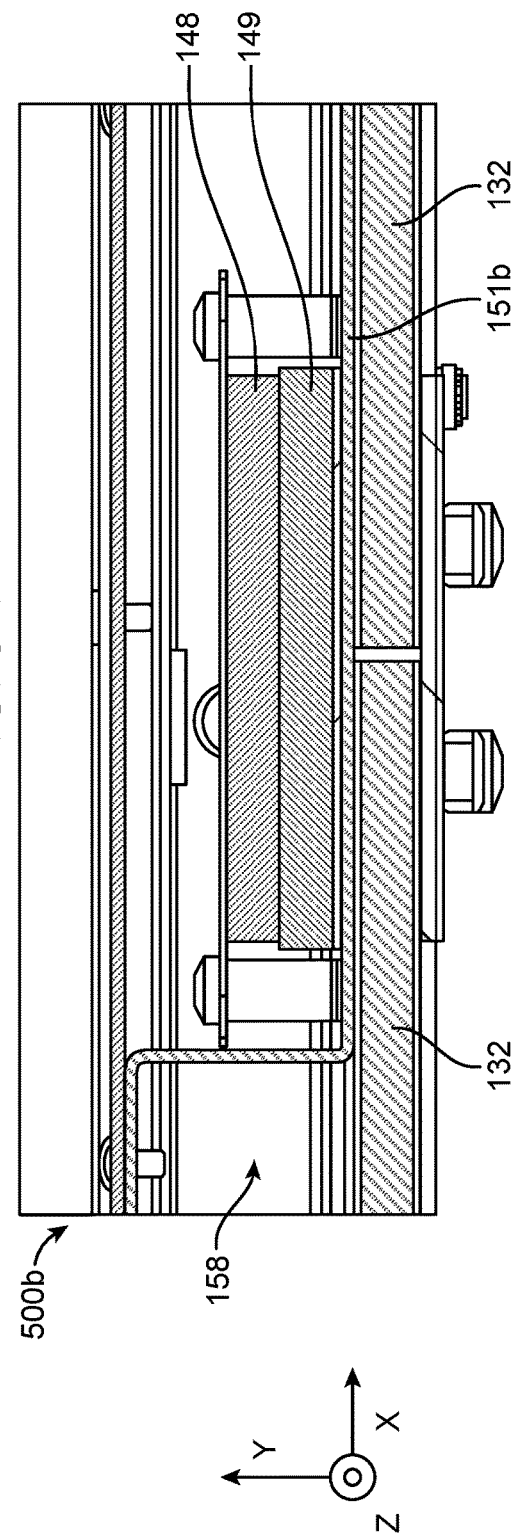

X-RAY SHIELDING DEVICE

BACKGROUND

This specification relates to X-ray computed tomography (CT) devices.

X-ray computed tomography (CT) is a technique that can be used by manufacturers in order to determine the quality of the products which they produce. X-ray CT is particularly useful to give manufacturers the ability to inspect certain parts of their products in a non-invasive, non-destructive fashion. Given this, X-ray CT is becoming more popular in production manufacturing settings where quality control is of high importance.

X-ray CT devices require shielding to prevent harmful X-rays from leaking from the X-ray CT device.

SUMMARY

This specification describes technologies relating to an X-ray shielding device. In particular, this specification describes systems and apparatuses configured to allow shielding of X-rays to prevent the emission of harmful X-rays.

Compared to other metals and materials in general, lead is one of the most effective X-ray shielding materials, owing to its large attenuation coefficient and high density. Additionally, lead is relatively inexpensive compared to other X-ray shielding materials. Lead, however, is toxic to humans and other species, and poses other engineering problems. For example, due to its softness, obtaining a precisely aligned structure composed of lead can require iterative assembly processes, which can be slow and cumbersome. Additionally, since lead is heavy, panels of lead making up the exterior of an X-ray shielding device might require being split up into smaller panels for assembly. The panels being split up into neighboring, smaller panels create gaps in the X-ray shielding device, which increases the chance of X-ray radiation leaking from the X-ray shielding device.

The described X-ray shielding device overcomes the challenges of working with lead through use of a datum structure to provide accurate mounting features that pass through the lead, thereby avoiding the use of lead for providing structural support. Additionally, in some implementations, a C-channel (or similarly shaped) structure within the X-ray shielding device can seal gaps between neighboring lead panels and reinforce an interior frame structure of the X-ray shielding device.

In general, innovative aspects of the subject matter described in this specification can be embodied an X-ray device that includes: an X-ray source configured to emit X-rays; a scintillator arranged to absorb the X-rays after interaction with an object that has been placed in the X-ray device, the scintillator being configured to emit light in response to absorption of the X-rays; a detector arranged to receive the light from the scintillator; a frame enclosing the X-ray source and the detector; standoffs positioned on the frame; shielding panels comprising lead; one or more brackets with fasteners configured to attach to the standoffs; and exterior panels with fasteners configured to attach to the one or more brackets. The standoffs form a datum structure for the one or more brackets. Each of the standoffs can have a length and a cross-sectional size, and each of the shielding panels can include holes having a cross-sectional size that is greater than the cross-sectional size of the standoffs by an amount that ensures the standoffs will pass through the holes despite variations in a placement of the holes in a given shielding panel resulting from manufacturing of the given shielding panel. The length of the standoffs can be greater than a maximum thickness possible for the given shielding panel due to variations in thickness resulting from the manufacturing of the given shielding panel.

Another general aspect can be embodied in an X-ray device that includes: an X-ray source configured to emit X-rays; a scintillator arranged to absorb the X-rays after interaction with an object that has been placed in the X-ray device, the scintillator being configured to emit light in response to absorption of the X-rays; a detector arranged to receive the light from the scintillator; a frame enclosing the X-ray source and the detector; shielding panels including lead; a metal piece having fasteners configured to attach the metal piece with the frame; and the shielding piece being sized and positioned to prevent X-rays from passing (i) through the gap and (ii) through the holes in the first and second shielding panels on either side of the gap, which are usable when coupling the first and second shielding panels with the frame. Each of the shielding panels can include holes usable to couple the shielding panel with the frame, where a first and a second of the shielding panels protect a single side of the frame and have been reduced in size to facilitate installation of the first and second shielding panels. A gap can remain between the first shielding panel and the second shielding panel when installed on the single side of the frame, and the metal piece can be shaped to receive a shielding piece including lead.

These and other implementations can each optionally include one or more of the following features. In some implementations, the X-ray device includes at least one additional shielding panel without lead.

In some implementations, the X-ray device further includes at least one corner guard including an angled sheet of lead extending between two adjacent sides of the frame. The angled sheet of lead can be placed at an acute angle between the two adjacent sides of the shielding panels, and edges of the angled sheet of lead can be chamfered in accordance with the acute angle.

In some implementations, the X-ray device further includes a metal sheet on which the corner guard is attached. The metal sheet can be attached to the frame In some implementations, the shielding panels comprise at least one laminate comprising lead and steel. In some implementations, each of the shielding panels is a laminate comprising lead and steel.

In some implementations, at least one of the one or more brackets is configured and arranged to have two of the exterior panels located on different sides of the X-ray device attached to a same bracket.

In some implementations, the X-ray device includes one or more additional shielding panels including a plastic impregnated with lead-free particles.

In some implementations, each of the standoffs includes a threaded hole, and each of the fasteners is configured to attach the brackets to the standoffs is a bolt configured to mate with the threaded hole.

In some implementations, each shielding panel of the shielding panels weighs less than 39 kilograms.

In some implementations, the cross-sectional size of the holes is greater than the cross-sectional size of the standoffs by about 35%. In some implementations, a cross-sectional size of the threaded holes is greater than a cross-sectional size of the standoffs by about 35%.

In some implementations, a shape of the holes in the shielding panels is a rounded rectangle.

In some implementations, the standoffs are arranged on at least two sides of the frame, thereby forming the datum structure in at least two intersecting planes of three-dimensional space.

In some implementations, neighboring edges of first and second shielding panels of the shielding panels form a gap. The X-ray device can further include: a metal piece having fasteners configured to attach the metal piece with the frame; and the shielding piece being sized and positioned to prevent X-rays from passing (i) through the gap and (ii) through holes in the first and second shielding panels on either side of the gap, which are usable to couple the first and second shielding panels with the frame. The metal piece can be shaped to receive a shielding piece including lead.

In some implementations, the X-ray device further includes additional shielding disposed on the shielding.

In some implementations, the X-ray device further includes corner guards including angled sheets of lead extending between two adjacent faces of the shielding panels. The corner guards can be angled at an acute angle between the two adjacent faces of the shielding panels, and edges of the corner guards are chamfered at the acute angle.

In some implementations, the X-ray device further includes a sheet on which each corner guard of the corner guards is attached. The sheet can be attached to the frame.

In some implementations, the X-ray device further includes brackets and standoffs. The standoffs can include threaded holes, and fasteners that attach the brackets to the standoffs can be bolts configured to mate with the threaded holes in the standoffs.

Particular embodiments of the subject matter described in this specification can be implemented to realize one or more of the following advantages. The systems and apparatuses described can provide highly efficient X-ray shielding, while preventing direct contact with lead by a user. Further, the design and assembly process can be quicker and less expensive by avoiding iterative processes for assembling the X-ray shielding device.

In some implementations, the systems and apparatuses described can be assembled without iterative processes, thereby reducing resources, e.g., equipment and time, to create a CT device and increasing a scalability of the CT device. For example, the exterior panels can be more robustly mounted with reduced clearance compared to assemblies without the datum structure. The more robustly mounted exterior panels can have a reduced likelihood of shifting during shipment or use. As another example, the CT device can accommodate larger objects for scanning if the size can be increased without increased error in alignment.

The details of one or more embodiments of the subject matter described in this specification are set forth in the accompanying drawings and the description below. Other features, aspects, and advantages of the invention will become apparent from the description, the drawings, and the claims.

BRIEF DESCRIPTION OF THE DRAWINGS

FIGS. 3A-3C respectively show perspective, cross-sectional, and close-up views of standoffs from the X-ray shielding device of FIG. 1A.

FIGS. 4A and 4B are perspective and close-up views of the brackets from the X-ray shielding device of FIG. 1A.

FIGS. 4C and 4D are cross-sectional views of the shielding panels and brackets of FIGS. 4A and 4B.

FIGS. 5A and 5B show cross-sectional views of examples of a metal piece having fasteners configured to attach the metal piece with the frame within the X-ray shielding device of FIG. 1A.

Like reference numbers and designations in the various drawings indicate like elements.

DETAILED DESCRIPTION

Figure 1A:
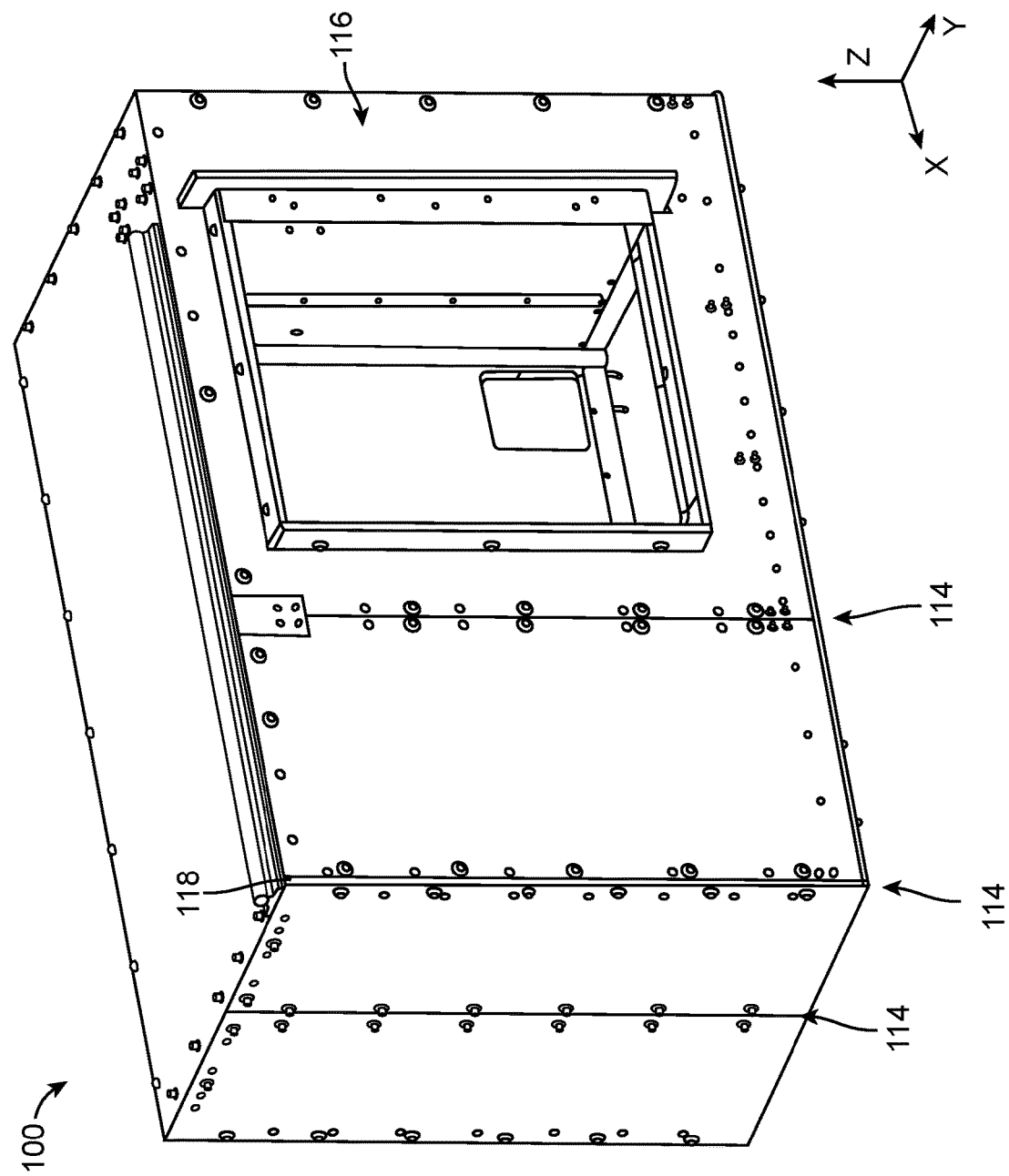
FIG. 1A shows a perspective view of an example of an X-ray shielding device.

FIG. 1A shows a perspective view of an example of an X-ray shielding device 100. The X-ray shielding device 100 can enclose a system that generates X-rays and prevents the generated X-rays from escaping from the X-ray shielding device 100. Panels made from lead, which is one of the most efficient X-ray absorbing materials, can surround the system. However, there are gaps 114 where panels are joined together, e.g., between panels on the same face 116 of the X-ray shielding device 100 and at corners 118 of the X-ray shielding device 100.

Although obtaining efficient X-ray shielding does not require the X-ray shielding device 100 to be perfectly sealed, e.g., since the X-rays may only travel in certain directions based on the geometry of the X-ray shielding device 100 and the enclosed system, adding shielding in front of the gaps 114 between panels of lead can improve the shielding efficiency. However, using lead to support structural components presents problems, due to lead's heaviness and softness. Accordingly, the present disclosure describes a datum structure for assembling an X-ray shielding device 100 that does not use lead for structural support, as well as a metal piece with additional shielding that also provides additional structural support.

Figure 1B:
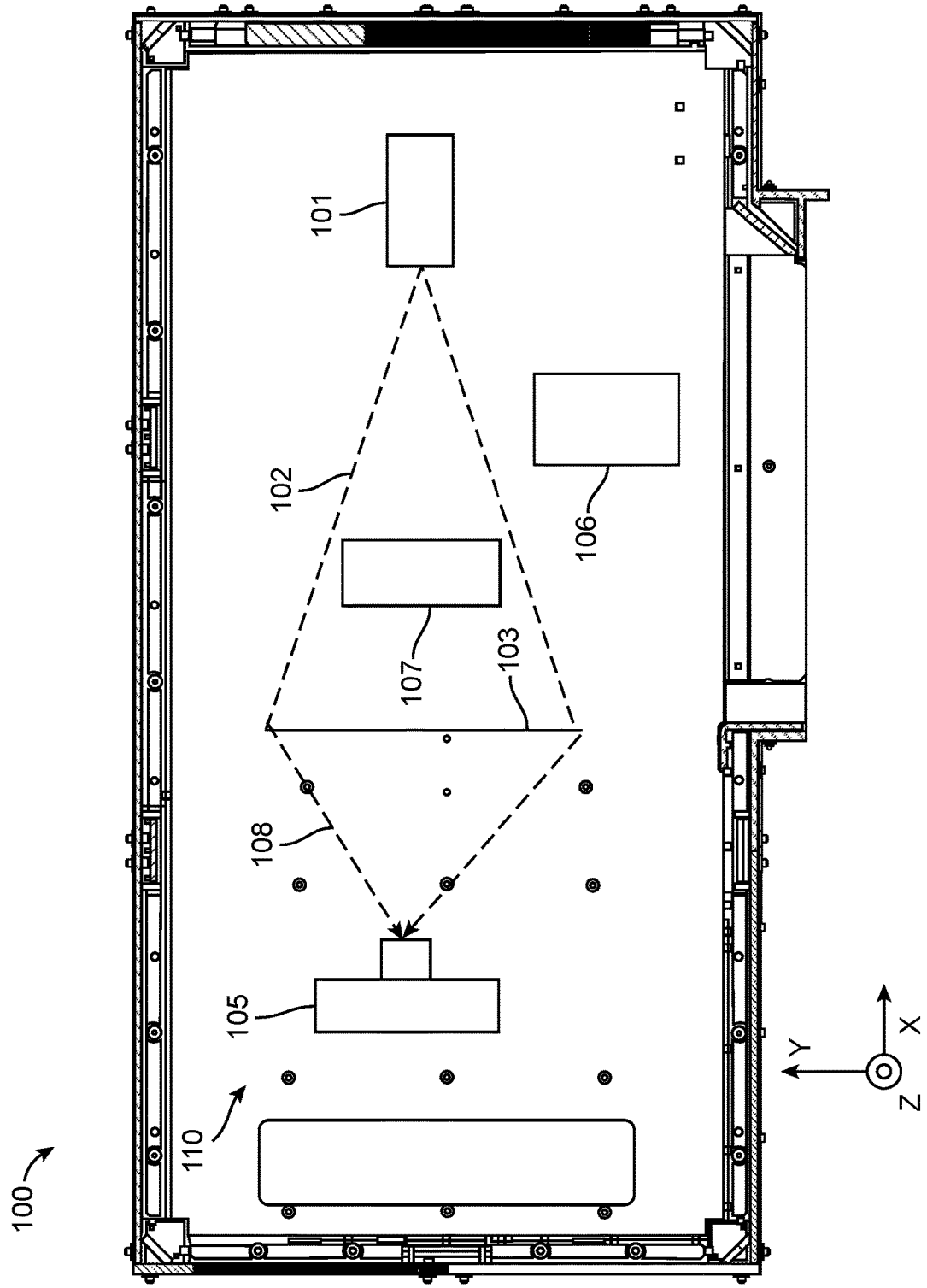
FIG. 1B shows a cross-sectional and schematic view of an example of an X-ray computed tomography system within the X-ray shielding device of FIG. 1A.

FIG. 1B shows a cross-sectional and schematic view of an example of an X-ray computed tomography system 110 within the X-ray shielding device 100 of FIG. 1A. The X-ray computed tomography system 110 includes X-ray source 101 configured to emit X-rays 102 towards scintillator 103. As X-rays 102 pass through scan target 107 and collide with scintillator 103, scintillator 103 absorbs the X-rays 102 and emits visible light 108, which generates an image. In some implementations, X-ray computed tomography system 110 can include one or more mirrors, e.g., folded optics, to reduce the optical path length and thus size of the X-ray shielding device 100.

In various example implementations, the X-ray computed tomography system 110 may include motion system 106 configured to move, reposition, manoeuvre, or otherwise manipulate the detector 105 and/or scan target 107 relative to the X-ray source 101. Furthermore, X-ray computed tomography (CT) system 110 may be an X-ray CT device. In various examples, X-ray source 101 may emit an X-ray beam, which may be a pencil beam, fan beam, cone beam, etc.

The shielding efficiency can be defined as the total energy of X-rays that escape the X-ray shielding device divided by the total energy of radiation produced by the X-ray source. For example, in some implementations, X-ray shielding device 100 only lets escape about one millionth of the energy of the generated X-rays. In some implementations, the shielding efficiency is selected to comply with regulations of the United States Food and Drug Administration (FDA) with a margin, e.g., stricter than the regulations.

Figure 2A:
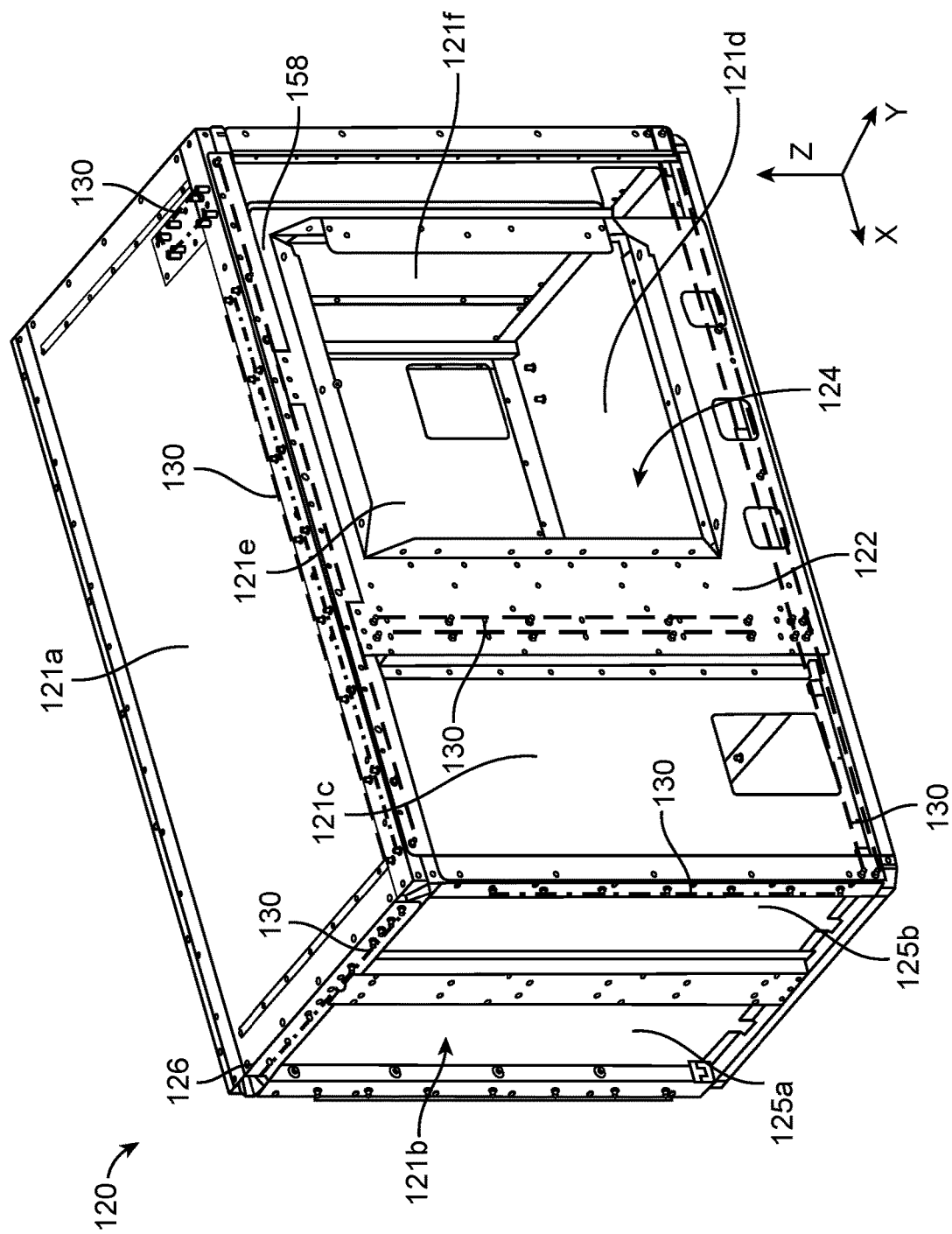
FIG. 2A shows a perspective view of an example of a frame and a datum structure of the X-ray shielding device of FIG. 1A.

FIG. 2A shows a perspective view of an example of a frame 120 and a datum structure 130 of the X-ray shielding device 100 of FIG. 1A. The frame 120 can include multiple sheets of metal, such as steel, that form six faces 121a, 121b, 121c, 121d, 121e, and 121f of the frame 120. In some implementations, the frame has a rectangular prism shape, with top, bottom, and side faces.

In some implementations, at least some of the faces 121a-f have indents formed by the sheets of metal not being completely planar, e.g., face 121b includes two sheets 125a and 125b, each of which include at least two 90° bends on the surface of the sheet. These bends can increase a stiffness of the sheets of metal, thereby turning them into structural components. At least some of the faces 121a-f can have an indent that creates space for fasteners between the frame 120 and exterior components.

The sheets of metal forming faces 121a-f can each have holes 126, through which fasteners can extend. In some implementations, the holes 126 are threaded to mate with threaded fasteners.

The datum structure 130 is marked by the dashed lines to indicate the linear alignment of standoffs 128, which in combination with the spacing between standoffs, makes the standoffs a datum structure 130. In some implementations, the standoffs 128 can be pressed into sheet metal or be blind, through hole, and/or threaded standoffs. For example, standoffs 128 can be pressed into sheet metal of the frame 120 by a sheet metal fabricator. With sufficient force, the standoffs 128 bond to the sheet metal and permanently remain in place. In some implementations, the standoffs 128 are threaded to mate with the frame 120.

The datum structure 130 defines various points for aligning the frame 120 with the panels of the X-ray shielding device 100 and other components such as brackets and rails, e.g., holes in each of the sheets of metal forming the frame and panels being aligned and components of the datum structure 130 passing through the holes.

The datum structure 130 aids in the alignment of the exterior panels of the X-ray shielding device 100, which will be discussed in reference to FIGS. 4A-4D. In other words, the datum structure 130 can be three-dimensional, and the standoffs 128 forming the datum structure 130 can be arranged in at least three intersecting planes. In some implementations, the datum structure 130 can be arranged in fewer than three intersecting planes, e.g., two parallel planes or two intersecting planes.

At least one of the sheets 122 making up a side face can include an opening 124 for a door for letting objects pass within and out of the X-ray shielding device 100.

Figure 2B:
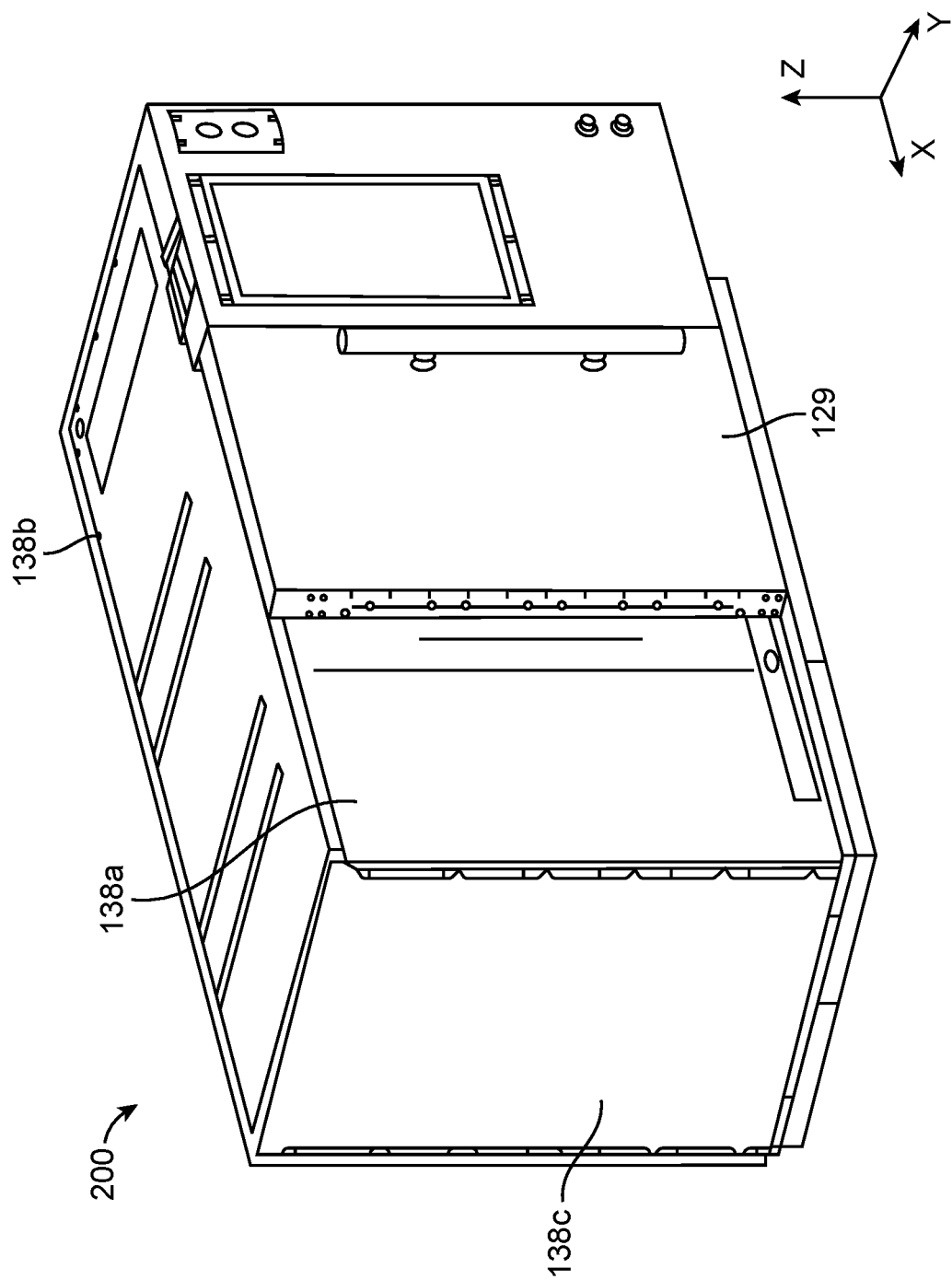
FIG. 2B shows a perspective view of an example of exterior panels of the X-ray shielding device of FIG. 1A with a door.

FIG. 2B shows a perspective view 200 of an example of exterior panels 138a, 138b, and 138c of the X-ray shielding device 100 of FIG. 1A with a door 129. The exterior panels 138 are made from a material other than lead, so that it is safe for human contact. In some implementations, the exterior panels 138a-c include metal, plastic, and/or other materials FIGS. 3A-3C respectively show perspective and cross-sectional views 300a, 300b, and 300c of standoffs 128 passing through shielding panels 132 (which can include lead in various forms) from the X-ray shielding device 100 of FIG. 1A. In perspective view 300a, the standoffs 128 pass from the frame 120 and through the shielding panels 132.

In some implementations, the shielding panels 132 include lead or a lead-free shielding material, e.g., a plastic impregnated with X-ray absorbing particles. For example, most of the shielding panels 132 can be pure lead or lead sandwiched between two layers of another material, and the remaining shielding panels can be lead-free. For example, lead-free, secondary shielding panels can cover portions of shielding panels 132 that include lead but have small leaks, such as holes or seams.

Due to the high density of lead, panels made from pure lead can be prone to bending and drooping along the direction of gravity while being assembled. To reduce the weight of the X-ray shielding device 100 and to avoid uneven shielding panels 132, the size and thus weight of the shielding panels 132 can be limited. For example, some or all the shielding panels 132 can be less than a limiting weight of between 20 and 40 kilograms, e.g., less than 23 or 39 kilograms. In order to maintain the weight of each shielding panel 132 below a threshold, a single face 131 can include multiple shielding panels 132. The specific weight limit can depend on the average strength of the workers in a given country, the workers' health and safety regulations in a given country, or both.

Although steel and lead provide important characteristics, e.g., structural support and X-ray absorption, respectively, manufacturing laminates of steel and lead can be less precise compared to other metals. Accordingly, providing a nonzero tolerance for interconnecting lead and steel laminates can facilitate aligning the lead and steel laminates The standoffs 128 pass through holes in the shielding panels 132, where the holes are sized to provide a tolerance for the standoffs. For example, as depicted in cross-sectional view 300b, holes 134 in the shielding panels 132 can be slots with a 11 mm width $W_1$ along the Y axis, and the standoffs 128 can have a rounded-rectangular cross-section with a 7.12 mm width $W_2$ along the Y axis, providing a radial clearance C of about 2 mm relative to the slot-shaped hole 134. In some implementations, the radial clearance is determined by percentage of the standoff 128, e.g., the holes 134 in the shielding panel 132 are sized to provide a percentile radial clearance of the width of the standoff 128, e.g., 35% of the width of the standoff 128. In some implementations, there is also a radial clearance for the standoffs 128 relative to the holes in the shielding panels 132 along a direction perpendicular to the width, e.g., the Z axis.

Using slots in the shielding panels 132, e.g., a rounded rectangle with a longest edge along the direction of the gap (Y axis in this example), can provide more lateral tolerance compared to using circular holes. If the cross-sectional size of the holes 134 is greater than the cross-sectional size of the standoffs 128 by a certain amount, e.g., 2 mm, the standoffs 128 will pass through the holes 134 despite variations in placement of the holes 134 in a given shielding panel 132 resulting from manufacturing of the given shielding panel 132.

As another example, each of the standoffs 128 and the holes 134 in the shielding panels 132 can have a circular cross-section, where the radius of the cross-section of the holes in the shielding panels 132 is greater than the radius of cross-section of the standoffs 128.

To connect the shielding panels 132 to the frame 120, the standoffs 128 must be long enough to at least pass through the shielding panels 132. As shown in cross-sectional view 300c, the standoff 128 has a first length $L_1$ along the X axis that is greater than a second length $L_2$ of the shielding panel 132 along the X axis, such that the standoff 128 can pass through the shielding panel 132 to connect the exterior panel 138 to the frame 120.

As indicated by the different widths along the X direction of an exterior end 128a of a standoff and an interior end 128b of a standoff, the exterior end 128a of the standoff can be long enough to attach to an exterior panel 138 through a bracket, while the interior end 128b of the standoff is nearly flat after having been pressed into the sheet metal of the frame 120. In some implementations, the interior end 128b of the standoff has a polygonal, e.g., hexagonal, cross section, e.g., along the X axis in FIG. 3C, to prevent rotation of the standoff 128.

In some implementations, the shielding panel 132 is a laminate, e.g., made of one or more materials, such as at least two materials bonded together to form a laminate. For example, shielding panel 132 can be a laminate formed by a lead layer 136a sandwiched by layers 136b with adhesive 305 at the interface between the lead layer 136a and the layers 136b. Layers 136b can be made from a material stiffer than lead, e.g., steel, to provide extra structural support. When the shielding panel 132 is a laminate, the length $L_1$ of the standoff 128 can be greater than the second length $L_2$ of the shielding panel 132 including the length of the layers 136b. When the shielding panel 132 is a single layer of lead, the length $L_1$ of the standoff 128 can be greater than a third length $L_3$ of lead layers 136a.

In general, the length $L_1$ of the standoff 128 is greater than the shielding panel 132, including when the shielding panel 132 includes one or more laminates 136, to ensure that the brackets for the exterior panels 138 do not touch the shielding panels 132. Accordingly, the location of the brackets for the exterior panels 138 and the exterior panels 138 are not affected by variations in the thickness and/or flatness of the shielding panels 132.

The laminates 136 can be sheets substantially parallel to the shielding panels 132. The cross-sectional size of the laminates 136 can be approximately the same as the shielding panels 132, e.g., smaller than the shielding panels 132 by about 0.5 millimeters. In some implementations, the laminate 136 is attached to the shielding panel 132 with an adhesive 305.

The length of the standoffs $L_1$ is greater than a maximum thickness possible for the given shielding panel, e.g., length $L_2$, due to variations in thickness resulting from the manufacturing of the given shielding panel. In some implementations, the length $L_2$ of the shielding panel 132 along the X axis can be relatively even, e.g., the same within 0.5 millimeters. Due to lead's softness, lead is relatively easy to machine lead panels of various thicknesses.

Figure 3D:
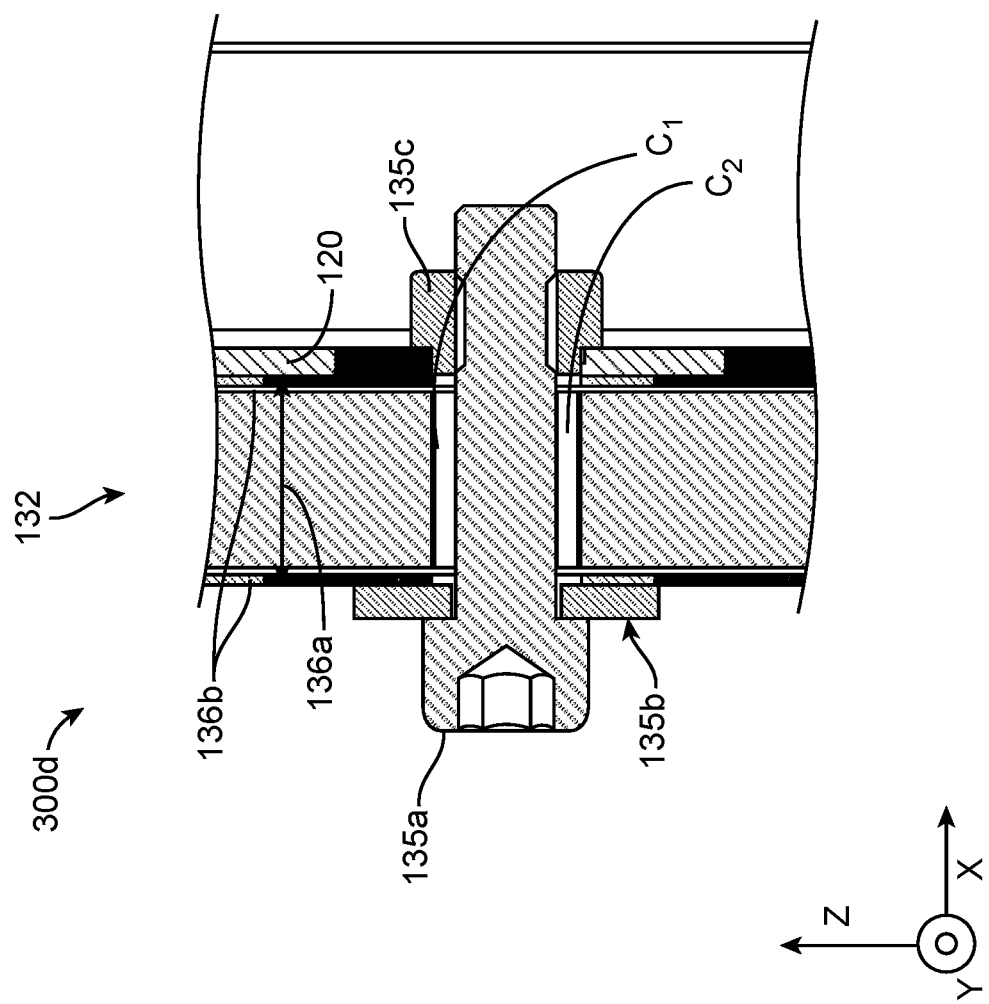
FIG. 3D shows a cross-sectional view of a shielding panel of the X-ray device of FIG. 1A held in place by fasteners.

FIG. 3D shows a cross-sectional view 300d of a shielding panel 132 of the X-ray device of FIG. 1A held in place by fasteners 135a. Fasteners 135a are located around the perimeter of each shielding panel 132 as depicted in FIG. 3A. In FIG. 3A, the standoffs 128 are represented by smaller circles, and larger circles correspond to washers 135b with a raised center corresponding to the fasteners 135a.

The holes 134 in shielding panel 132 can have a variety of purposes. For example, some of holes 134 are sized and arranged to allow standoffs 128 to couple to the frame 120 to brackets 140 for mounting the exterior panels 138, and some of holes 134 are sized and arranged to allow fasteners 135a to couple the shielding panels 132 to the frame 120.

As depicted in FIG. 3D, a fastener 135a, such as a bolt, extends completely through the shielding panel 132 to attach to the frame 120. In this example, the shielding panel 132 is a laminate with a lead layer 136a sandwiched by layers 136b. The washers 135b are on an exterior side of the shielding panel 132 and surround the fastener 135a. Washers 135b distribute the load of fastener 135a on the shielding panel. Fasteners 135c are on an interior side of the of the shielding panel 132 and surround the fastener 135a. In some implementations, fasteners 135c are nuts pressed into the sheet metal of the frame 120.

Given the difficulty with precisely manufacturing lead shielding panels 132, the holes 134 in the shielding panels and fasteners 135a are sized to provide a clearance around the fastener 135a. In FIG. 3D, clearances $C_1$ and $C_2$ are the vertical clearances, e.g., along the Z axis, above and below, respectively, between the fastener 135a and hole 134 of the shielding panel 132. In some implementations, there is a clearance between the fasteners 135a and holes 134 in either one or both of the horizontal directions.

FIGS. 4A and 4B are perspective and close-up views 400a and 400b of brackets 140 from the X-ray shielding device 100 of FIG. 1A. The datum structure 130 provides mounting locations for precisely mounting brackets 140, as well as door motion and locking components. The brackets 140a-140g can hold the exterior panels 138 (pictured in FIG. 2B) in place, e.g., attached to the frame 120 via fasteners, such as standoffs or bolts. Each bracket 140 can attach to at least two exterior panels 138. Bracket 140c can include holes that precisely align with the datum structure 130, such that standoffs 128 can extend from the frame 120 through the shielding panels 132 to mount the brackets. Using the datum structure 130 can also increase the repeatability of methods of accurately aligning the various components of the X-ray shielding device 100.

In some implementations, as depicted in close-up perspective view 400b, some of the brackets, e.g., brackets 140a, 140b, 140f and 140g, include edges 143a and 143b that meet at a right angle to attach exterior panels 138 that meet at a right angle. One of the edges, e.g., edge 143a, can be ridged. In some implementations, some brackets, e.g., bracket 140g can hold two exterior panels, e.g., exterior panels 138a and 138c, with different orientations while only being attached to standoffs 128.

In some implementations, the X-ray shielding device 100 includes door guide rails 142, which are configured to allow a sliding door, e.g., door 129, to slide along a horizontal direction, e.g., the X axis in this example, to both cover and uncover the opening 124. Additionally, the X-ray shielding device 100 can include a door interlock 144, which locks the sliding door into place when covering the opening 124. When the sliding door is latched into place by the door interlock 144, the sliding door is in a position that reduces X-ray leakage compared to other positions.

FIGS. 4C and 4D are cross-sectional and close-up views 400c and 400d of the shielding panels and brackets of FIGS. 4A and 4B. As can be seen in both views 400c and 400d, the bracket 140 is attached to standoffs 128, which in turn are part of the frame 120. A small gap 145, e.g., 1.5-3 mm, allows for variation in the thickness and flatness tolerance deviations of the shielding panel 132 without affecting the position of the bracket 140. The size of the gap 145 depends on material thicknesses of the shielding panels 132 and length(s) of the standoffs 128.

FIGS. 5A and 5B show cross-sectional views 500a and 500b of examples of a metal piece having fasteners configured to attach the metal piece with the frame 120 within the X-ray shielding device 100 of FIG. 1A. The metal piece provides mounting locations for the shielding panels 132 in addition to the mounting locations of the datum structure 130 at corners of the X-ray shielding device 100.

In some implementations, the metal piece is a C-channel 150, e.g., a continuous piece of metal and is called a "C"-channel for having a shape like the letter "C." For example, the C-channel 150 can be composed of two parallel segments 151a 151c (extending in a first direction) connected by a segment 151b (extending in a second direction) perpendicular to both segments 151a and 151c and connected at the edges of segments 151a and 151c.

In general, the metal piece can have various shapes as long as the shape creates room to receive the additional shielding 148 and includes at least one surface by which the metal piece attaches to the frame 120. For example, the shape and location of the metal piece can be selected to cover holes 134 in the shielding panels 132 for fasteners 135a and standoffs 128.

An advantage of using the C-shape is there are two locations where the metal piece attaches to the frame 120 on either side of the additional shielding 148 e.g., to the left and right of and below additional shielding 148 in FIG. 5A. As a result, a C-shaped metal piece adds structural support and strength to the frame 120 and facilitates holding of the weight of the main shielding panels 132.

The C-channel 150 can have associated fasteners, e.g., fastener 154, configured to attach the C-channel 150 to the frame 120. In some implementations, the fastener 154 passes through two aligned holes of the C-channel 150 and the frame 120.

The C-channel 150 can be disposed between shielding panels 132 and the frame 120 where gaps 147 between neighboring shielding panels 132 exist. Due to the shape of the C-channel 150, e.g., having two segments extending in the direction from the frame 120 to the shielding panels 132 (along the Y axis in this example) and another segment parallel to the direction of the gap 147 between the shielding panels 132 (along the X axis in this example), additional shielding 148 can be located between the frame 120 to the shielding panels 132 and block the gap 147.

The additional shielding 148 can be attached to a plate 152, which is configured to attach to the C-channel 150. For example, the plate 152 can define a hole through which a fastener 156 can pass and attach to the segment 151b of the C-channel 150. The plate 152 can be made of a metal stiffer than lead, e.g., steel. In some implementations, the additional shielding 148 can be directly attached to the C-channel 150 without the plate 152. However, when the additional shielding 148 includes lead, creating precise holes for fastening can be easier when using a stiffer metal compared to lead.

Figure 6A:
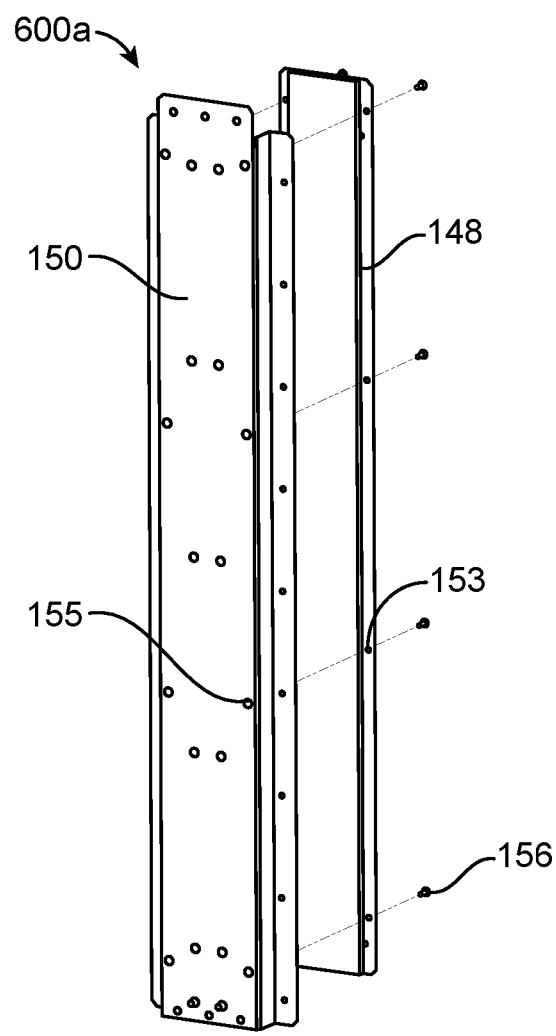
FIGS. 6A and 6B show exploded views of the C-channel and additional shielding of FIG. 5A.
Figure 6B:
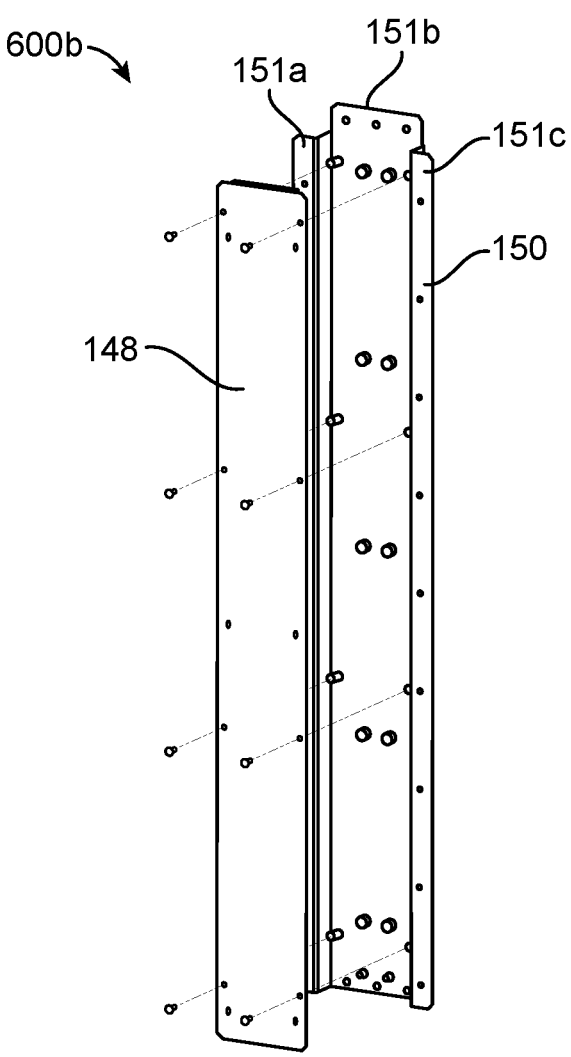

FIGS. 6A and 6B show exploded views 600a and 600b of the C-channel 150 and additional shielding 148 of FIG. 5A. FIGS. 6A and 6B depict the C-channel 150 and additional shielding 148 but flipped about the Y axis. As depicted in FIGS. 6A and 6B, the additional shielding fits between the two segments 151a and 151c of the C-channel 150. Holes 153 in the additional shielding 148 are aligned with holes 155 in the C-channel 150, such that fasteners 156 can connect the additional shielding 148 to the C-channel 150.

As visible in exploded views 600a and 600b, each of the first through third segments 151a-151c extends in the third direction perpendicular to both the first and second directions, e.g., a vertical direction along the Z axis in this example. The C-channel 150 can be long enough in the vertical direction to cover an entire gap between neighboring shielding panels 132.

FIG. 5B depicts a similar view as FIG. 5A, with some differences. First, this view is for different side of the X-ray shielding device 100, and therefore the orientation is flipped along the X axis. Second, the C-channel 158 extends longer along the X axis compared to C-channel 150. In this example, C-channel 158 extends far enough along the X axis to span the opening 124 for the door 129. With reference to FIG. 2A, the C-channel 158 is a part of the sheet 122, which includes an opening 124 for the door 129. Third, the C-channel 158 is attached to an additional layer of shielding 149, which contacts the exterior panels 138.

Figure 6C:
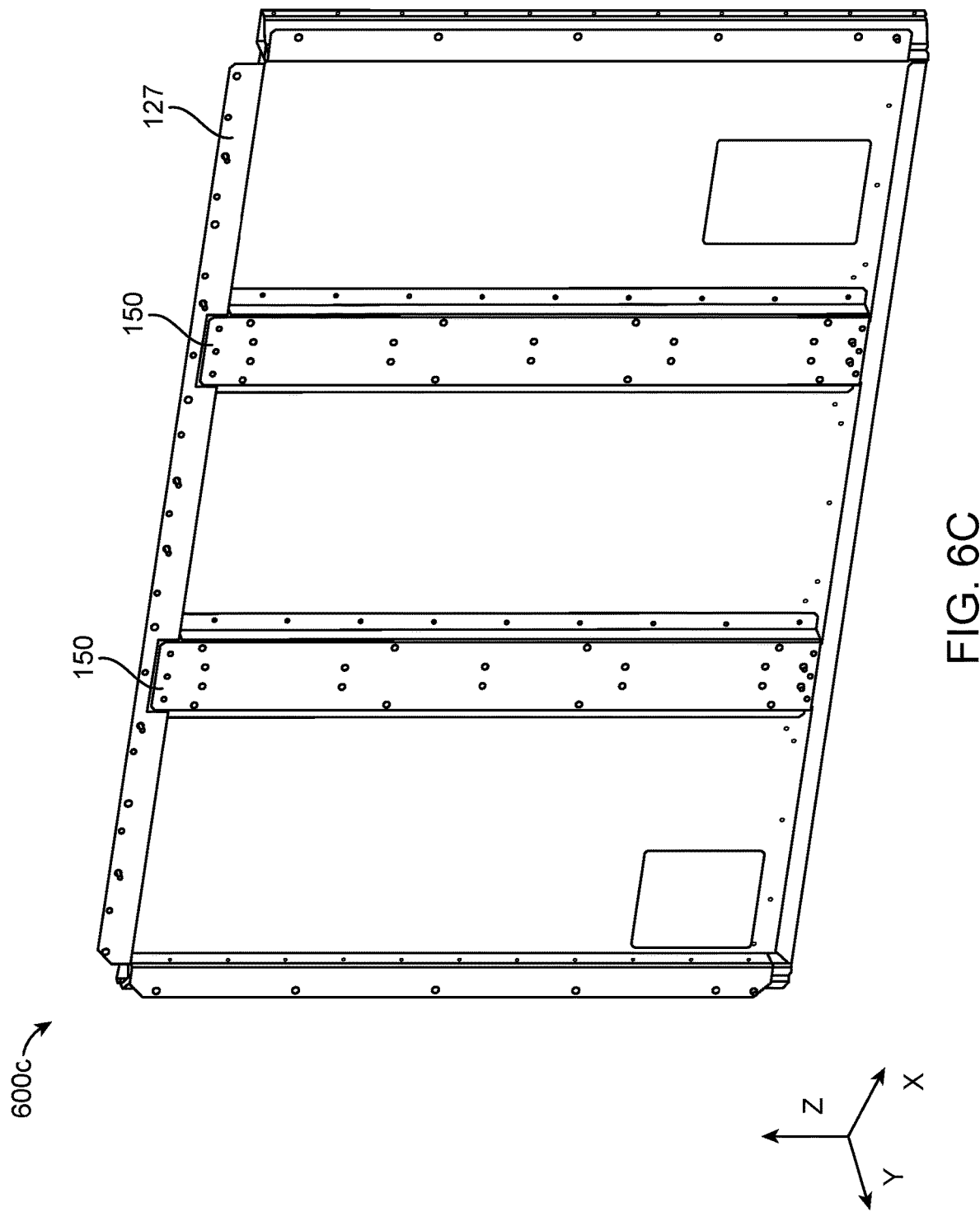
FIG. 6C depicts a perspective view of the C-channel of FIG. 5A riveted to a panel of the frame of FIG. 2A.

FIG. 6C depicts a perspective view 600c of the C-channel 150 of FIG. 5A riveted to a panel 127 of the frame 120 of FIG. 2A. The C-channel 150 being riveted to the panel 127 can provide structural reinforcement for the frame 120. In some implementations, the C-channel 150 is riveted to the panel 127 using flanges on both the top and bottom, e.g., along the Z axis, of the C-channel 150.

Figure 7:
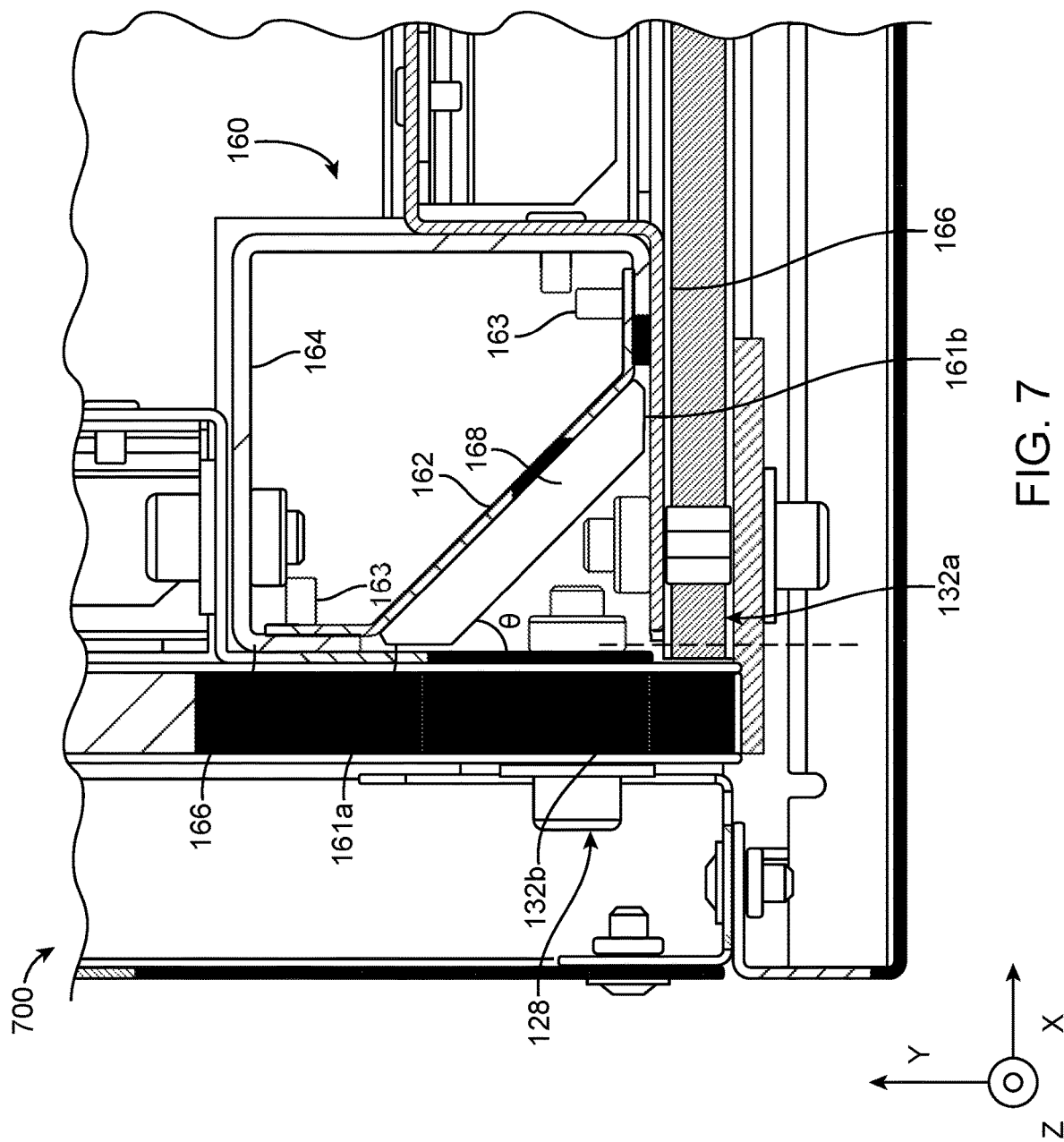
FIG. 7 shows a cross-sectional view of an example of a corner guard within the X-ray shielding device of FIG. 1A.

FIG. 7 shows a cross-sectional view 700 of an example of a corner guard 160 within the X-ray shielding device of FIG. 1A. Similarly to how the additional shielding 148 prevents strays X-rays from escaping through gaps between neighboring, parallel shielding panels 132, the corner guards 160 can absorb X-rays that would otherwise pass through gaps between neighboring, perpendicular shielding panels 132. The corner guards 160 can include an angled sheet of lead 168 or another shielding material.

In some implementations, the corner guard 160 includes a sheet 162, which is made of a metal stiffer than lead, such as steel. The sheet 162 can include holes configured to accept fasteners 163, which extend through both the sheets 162 and a member 164. The member 164 can have an open rectangular shape, e.g., a rectangle with portions from two adjacent sides missing at the point where the two adjacent sides would have met. The metal frame can include portions 166 that extend from neighboring, perpendicular panels of the frame 120, e.g., an L-shaped portion. The portion 166 can be shaped to receive a sheet 162, which is attached to member 164, of a corner guard 160. For example, the angled edges 161a and 161b of the angled sheet of lead 168 can be parallel to each of the L-shaped portions 166. The fasteners 163 can extend through the sheet 162, the member 164, and the portions 166 to attach the corner guards 160 to the frame 120. The sheet 162 and member 164 can be fastened together to form a more rigid and structural composite member.

In some implementations, the corner guards 160 are completely within the datum structure 130. In other words, the corner guards 160 are interior rather than exterior to the frame 120, e.g., enclosed by portions 166 of the frame 120. The angled sheet of lead 168 can be chamfered at an acute angle θ, e.g., 30° or 60°, relative to the portions 166. The corner guards can be placed in each of the four corners within the X-ray shielding device 100.

Referring to FIGS. 3B and 7, the gap between shielding panels 132a and 132b can be reduced by using slots as the shape for holes 134. Using slots allows for biasing the shielding panels 132 up against a blast wall, indicated by the dashed line in FIG. 7. For example, shielding panel 132a can slide further to the left, e.g., along the X axis, to reduce the gap between the blast wall, e.g., the interior side of the X-ray shielding device 100 receiving X-ray radiation directly from the X-ray source 101. Additionally, the metal piece, e.g., C-channel 150, can compensate, e.g., provide additional shielding, for any extra spacing created on the right side of the shielding panel 132a where it meets another shielding panel on the same face. Accordingly, in tandem, the datum structure 130 and the metal piece provide flexible alignment without reducing the shielding efficiency of the X-ray shielding device 100.

Although implementations with a C-channel for the metal piece and doubly chamfered corner guard have been described, other implementations are possible. For example, the metal piece can have a square, rectangular, or circular shape. As another example, the corner guard can have a rectangular shape with one corner being chamfered.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented using one or more modules of computer program instructions encoded on a non-transitory computer-readable medium for execution by, or to control the operation of, data processing apparatus. The computer-readable medium can be a manufactured product, such as a hard drive in a computer system or an optical disc sold through retail channels, or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM (Erasable Programmable Read-Only Memory), EEPROM (Electrically Erasable Programmable Read-Only Memory), and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display) display device, an OLED (organic light emitting diode) display device, or another monitor, for displaying information to the user, and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other. Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

While this specification contains many implementation details, these should not be construed as limitations on the scope of what is being or may be claimed, but rather as descriptions of features specific to particular embodiments of the disclosed subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desired results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims.

What is claimed is:

1. An X-ray device comprising:
   an X-ray source configured to emit X-rays;
   a scintillator arranged to absorb the X-rays after interaction with an object that has been placed in the X-ray device, the scintillator being configured to emit light in response to absorption of the X-rays;
   a detector arranged to receive the light from the scintillator;
   a frame enclosing the X-ray source and the detector;
   standoffs positioned on the frame, wherein each of the standoffs has a length and a cross-sectional size;
   shielding panels comprising lead, wherein each of the shielding panels includes holes having a cross-sectional size that is greater than the cross-sectional size of the standoffs by an amount that ensures the standoffs will pass through the holes despite variations in a placement of the holes in a given shielding panel resulting from manufacturing of the given shielding panel, and the length of the standoffs is greater than a maximum thickness possible for the given shielding panel due to variations in thickness resulting from the manufacturing of the given shielding panel;
   one or more brackets with fasteners configured to attach to the standoffs, wherein the standoffs form a datum structure for the one or more brackets; and
   exterior panels with fasteners configured to attach to the one or more brackets.

2. The X-ray device of claim 1, comprising at least one additional shielding panel without lead.

3. The X-ray device of claim 1, further comprising at least one corner guard comprising an angled sheet of lead extending between two adjacent sides of the frame, wherein the angled sheet of lead is placed at an acute angle between the two adjacent sides of the shielding panels, and edges of the angled sheet of lead is chamfered in accordance with the acute angle.

4. The X-ray device of claim 3, further comprising a metal sheet on which the corner guard is attached, wherein the metal sheet is attached to the frame.

5. The X-ray device of claim 1, wherein each of the shielding panels is a laminate comprising lead and steel.

6. The X-ray device of claim 1, wherein at least one of the one or more brackets is configured and arranged to have two of the exterior panels located on different sides of the X-ray device attached to a same bracket.

7. The X-ray device of claim 1, comprising one or more additional shielding panels comprising a plastic impregnated with lead-free particles.

8. The X-ray device of claim 1, wherein each of the standoffs comprises a threaded hole, and each of the fasteners is configured to attach the brackets to the standoffs is a bolt configured to mate with the threaded hole.

9. The X-ray device of claim 1, wherein each shielding panel of the shielding panels weighs less than 39 kilograms.

10. The X-ray device of claim 1, wherein the cross-sectional size of the holes is greater than the cross-sectional size of the standoffs by about 35%.

11. The X-ray device of claim 1, wherein a shape of the holes in the shielding panels is a rounded rectangle.

12. The X-ray device of claim 1, wherein the standoffs are arranged on at least two sides of the frame, thereby forming the datum structure in at least two intersecting planes of three-dimensional space.

13. The X-ray device of claim 1, wherein neighboring edges of first and second shielding panels of the shielding panels form a gap, and further comprising:
   a metal piece having fasteners configured to attach the metal piece with the frame, wherein the metal piece is shaped to receive a shielding piece comprising lead; and
   the shielding piece being sized and positioned to prevent X-rays from passing (i) through the gap and (ii) through holes in the first and second shielding panels on either side of the gap, which are usable to couple the first and second shielding panels with the frame.

14. An X-ray device comprising:
   an X-ray source configured to emit X-rays;
   a scintillator arranged to absorb the X-rays after interaction with an object that has been placed in the X-ray device, the scintillator being configured to emit light in response to absorption of the X-rays;
   a detector arranged to receive the light from the scintillator;
   a frame enclosing the X-ray source and the detector;
   shielding panels comprising lead, wherein each of the shielding panels includes holes usable when coupling the shielding panel with the frame, wherein a first and a second of the shielding panels protect a single side of the frame and have been reduced in size to facilitate installation of the first and second shielding panels, and wherein a gap remains between the first shielding panel and the second shielding panel when installed on the single side of the frame;

a metal piece having fasteners configured to attach the metal piece with the frame, wherein the metal piece is shaped to receive a shielding piece comprising lead; and the shielding piece being sized and positioned to prevent X-rays from passing (i) through the gap and (ii) through the holes in the first and second shielding panels on either side of the gap, which are usable to couple the first and second shielding panels with the frame.

15. The X-ray device of claim 14, further comprising additional shielding disposed on the shielding.

16. The X-ray device of claim 14, further comprising corner guards comprising angled sheets of lead extending between two adjacent faces of the shielding panels, wherein the corner guards are angled at an acute angle between the two adjacent faces of the shielding panels, and edges of the corner guards are chamfered at the acute angle.

17. The X-ray device of claim 16, further comprising a sheet on which each corner guard of the corner guards is attached, wherein the sheet is attached to the frame.

18. The X-ray device of claim 14, wherein the shielding panels comprise at least one laminate comprising steel and lead.

19. The X-ray device of claim 14, further comprising brackets and standoffs, wherein the standoffs comprise threaded holes, and fasteners that attach the brackets to the standoffs are bolts configured to mate with the threaded holes in the standoffs.

20. The X-ray device of claim 19, wherein a cross-sectional size of the threaded holes is greater than a cross-sectional size of the standoffs by about 35%.

\* \* \* \* \*